US00PP28875P2

(12) United States Plant Patent
Gerdts et al.

(10) Patent No.: US PP28,875 P2
(45) Date of Patent: Jan. 16, 2018

(54) PEACH TREE, 'BURPEACHFORTY'

(50) Latin Name: *Prunus persica*
Varietal Denomination: Burpeachforty

(71) Applicants: Timothy J. Gerdts, Kingsburg, CA (US); John K. Slaughter, Fresno, CA (US)

(72) Inventors: Timothy J. Gerdts, Kingsburg, CA (US); John K. Slaughter, Fresno, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 15/330,616

(22) Filed: Oct. 19, 2016

(51) Int. Cl.
*A01H 5/08* (2006.01)

(52) U.S. Cl.
USPC ..... Plt./197

(58) Field of Classification Search
USPC ..... Plt./197
CPC ..... A01H 5/0868; A01H 5/08; A01H 5/02; A01H 5/0856
See application file for complete search history.

*Primary Examiner* — June Hwu
(74) *Attorney, Agent, or Firm* — Randall Danskin P.S.

(57) ABSTRACT

A new and distinct variety of peach tree (*Prunus persica*), which is denominated varietally as 'Burpeachforty', and which further produces an attractively colored yellow fleshed, clingstone peach which is mature for harvesting and shipment approximately June 12 to June 19 under the ecological conditions prevailing in the San Joaquin Valley of central California.

2 Drawing Sheets

Latin name: *Prunus persica.*
Varietal denomination: Burpeachforty.

BACKGROUND OF THE NEW VARIETY

The present variety of peach tree resulted from an ongoing program of fruit and nut tree breeding. The purpose of this program is to improve the commercial quality of deciduous fruit and nut varieties, and rootstocks, by creating and releasing promising selections of *Prunus, Malus, Punica* and *Juglans* species. To this end we make both controlled and hybrid cross-pollinations each year in order to produce seedling populations from which improved progenies are evaluated and selected.

The seedling, 'Burpeachforty' was originated by us, and selected from a population of seedlings growing in our experimental orchards which are located near Fowler, Calif. The seedlings, grown on their own roots, were derived from planting seed of a controlled cross-pollination of an unnamed, non-patented, proprietary seedling which produces a yellow-fleshed, clingstone peach which was used as the female parent. The male or pollen parent, on the other hand, produced a sub-acidic, white-fleshed peach and is further varietally identified as 'Burpeachthirtyfive' (U.S. Plant Pat. No. 25,744). The resulting fruit from this cross-pollination was collected from the female parent at a mature stage, and seeds were extracted from this same fruit in June of 2007. After a period of stratification, the seeds were placed in our greenhouse by population, and then field planted for tree establishment, and ultimately to exhibit fruit for further evaluation. One yellow fleshed peach seedling, which is the present variety, exhibited especially desirable characteristics, and was then designated as 'Q13.052'. This seedling was marked for subsequent observation. After the 2010 fruiting season, the new variety of peach tree was selected for advanced evaluation and repropagation.

ASEXUAL REPRODUCTION

Asexual reproduction of this new and distinct variety of peach tree was accomplished by budding the new peach tree onto 30 trees which were established with 'Nemaguard' Rootstock (un-patented). This asexual reproduction was performed by us in our experimental orchard which is located near Fowler, Calif. Subsequent evaluations of these asexually reproduced trees have demonstrated to us that those asexual reproduced trees display all the characteristics as seen in the original plant. All characteristics of the original tree, and its fruit, were established, and appear to be transmitted through these succeeding asexual propagations.

SUMMARY OF VARIETY

'Burpeachforty' is a new and distinct variety of peach tree, which is considered of relatively large size, and which has a vigorous growth habit. This new tree is also a regular and productive bearer of relatively large, firm, yellow-fleshed, acidic clingstone fruit which have a very good flavor, and eating qualities. This new peach tree has a medium chilling requirement of approximately 500 hours, and further produces relatively uniformly sized fruit throughout the tree's canopy. In addition to the foregoing, the fruit of the new peach tree also appears to have good handling and shipping qualities. The 'Burpeachforty' peach tree bears fruit which are typically ripe for commercial harvesting, and shipment, on approximately June 12 to June 19 under the usual ecological conditions prevailing in the San Joaquin Valley of central California. In relative comparison to the 'June Flame' peach tree 'Burpeachsix' (U.S. Pat. No. 13,392), which is the closest known variety, the new variety of peach tree bears fruit that is clingstone by nature, whereas the 'June Flame' peach tree produces fruit which exhibits a freestone character. Further, the fruit produced by the new variety exhibits a more oblate, and less elongated shape than the fruit produced by the 'June Flame' peach tree when the fruit of this patented tree is used as the commercial comparative variety. In relative comparison to the unnamed, and unpatented seed parent tree, the new variety produces fruit which is considered as having non-melting flesh, whereas the seed parent produces fruit having a melting flesh character. The new variety differs from the pollen parent, in that, the current new variety produces fruit which is both yellow-fleshed, and further exhibits a classic acidic flavor, while, on the other hand, the pollen parent produces fruit which is sub-acidic. In addition to the foregoing, the new peach tree variety produces fruit which has a yellow-flesh, as compared to the pollen parent which produces fruit having a white-flesh.

Figure 1:
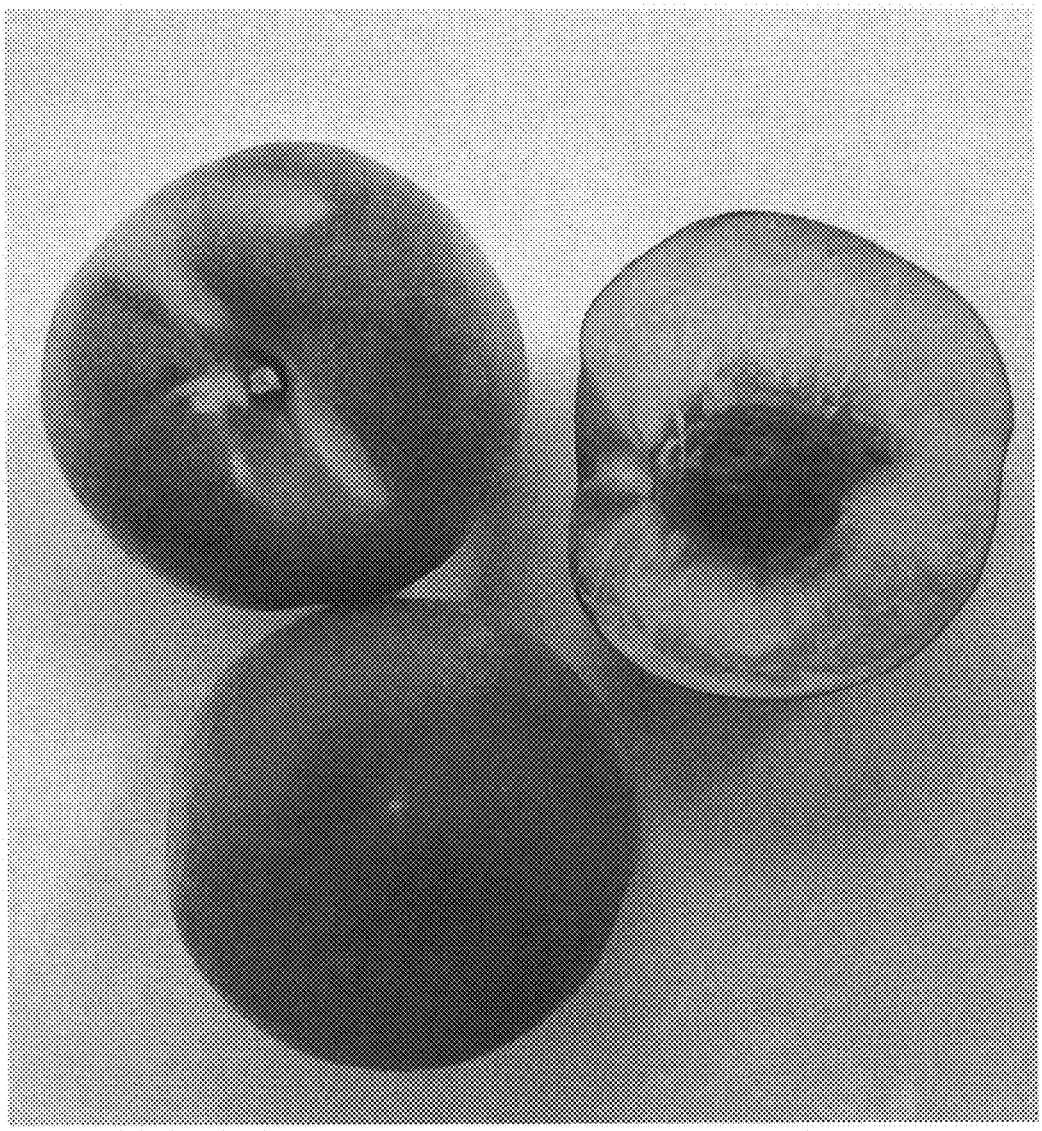
FIG. 1 which is provided, is a color photograph showing two whole mature fruit harvested from a tree which is five years old, and which displays both the apical and basal aspects thereof. Further, one mature fruit is shown and which is bisected in the suture or longitudinal plane, and which reveals the flesh color, and stone characteristics thereof. The external coloration of the fruit as shown in the photograph is sufficiently matured for harvesting and shipment.
Figure 2:
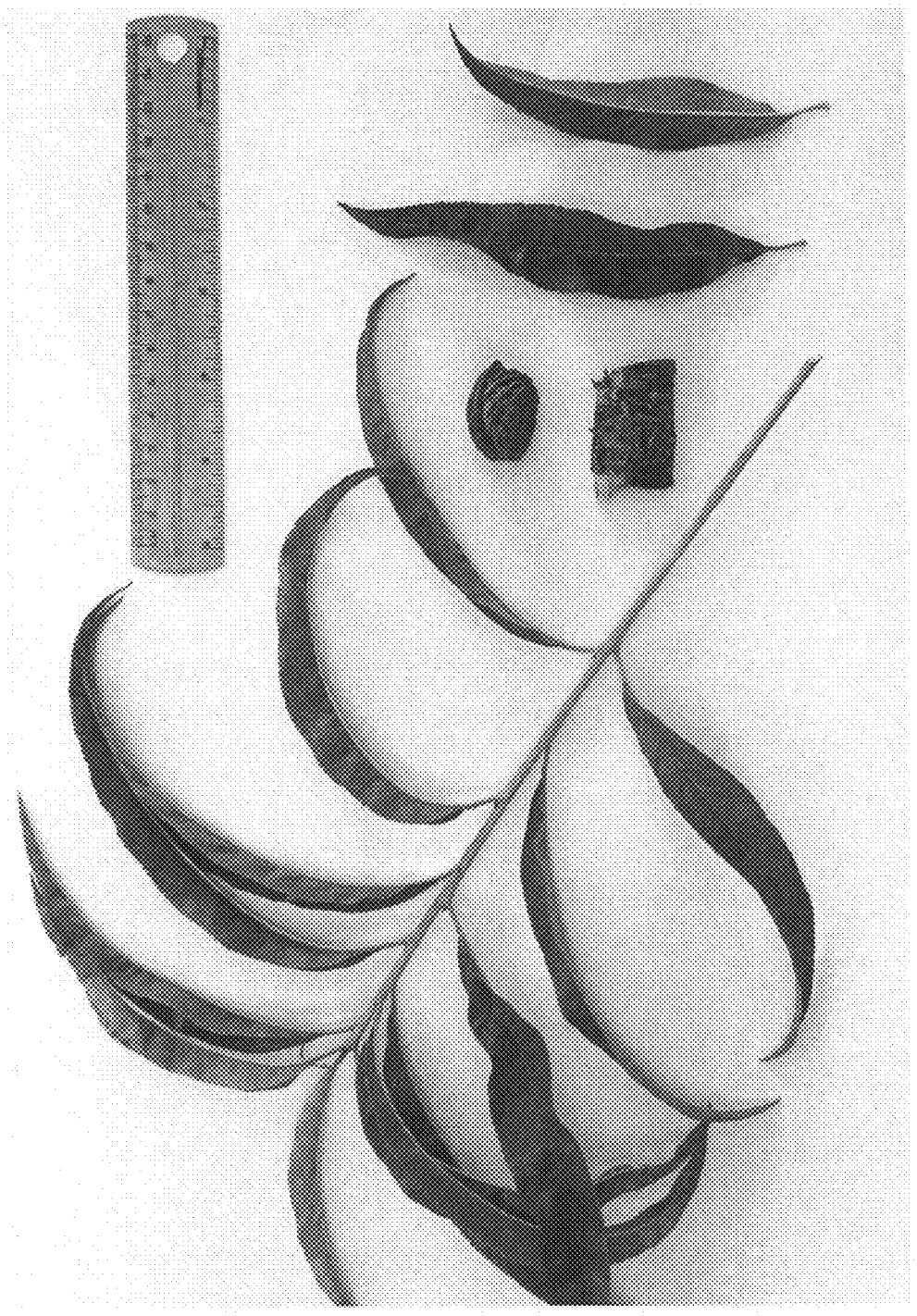
FIG. 2 displays a sample vegetative shoot bearing typical leaves; a small piece of bark which was taken from the trunk; and a typical stone with the flesh removed.

The colors in the aforementioned photographs are as nearly true as is reasonably possible in a color representations of this type. Due to chemical development, processing and printing, the leaves and fruit depicted in these photographs may, or may not, be accurate when compared to the actual specimen. For this reason, future color references should be made to the color plates (Royal Horticultural Society, Fourth Edition, 2001), and the descriptions as provided, hereinafter.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display all the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of peach tree, the following has been observed during the tenth fruiting season, and under the ecological conditions prevailing at the orchards of the assignee and which are located near the town of Fowler, county of Fresno, state of California. All major color code designations are by reference to The R.H.S. Color Chart (Royal Horticultural Society, Fourth Edition, 2001) and which are provided by The Royal Horticultural Society of Great Britain. Common color names are also occasionally used.

TREE

Size:

*Generally.*—Considered medium to medium-large in its growth pattern as compared to other common commercial peach cultivars ripening in the same season of maturity. The tree of the present variety was pruned to a height of approximately 270.0 cm. to about 310.0 cm. at commercial maturity.

Width: Approximately 265.0 cm.

Vigor: Considered moderately vigorous. The present peach tree variety grew from about 175.0 cm. to about 180.0 cm, in height, during the first growing season. The new variety of peach tree was pruned to a height of approximately 150.0 cm. during the first dormant season, and primary scaffolds were then selected for the desired tree structure.

Productivity: Productive. Fruit set varies from more than the desired crop load, to levels higher than the desired amounts, when the new variety is grown in a suitable horticultural zone, and under appropriate commercial nursery conditions. The fruit set is spaced, by thinning, to develop the remaining fruit into the desired market-sized fruit. The number of the fruit set varies with the prevailing climatic conditions, and the cultural practices employed.

Fruit bearing: Regular. Fruit set for the new variety has been more than adequate during the previous years of observation, and thinning of the canopy was necessary during the past 6 years on both the original seedling, and on subsequent asexually reproduced trees.

Tree form: Upright, and pruned into a vase shape.

Canopy density: Considered moderately dense. It has been discovered that pruning the branches from the center of the tree to obtain a resulting vase-shape allows for enhanced air movement, and appropriate amounts of sunlight to improve fruit color, and renewal of fruiting wood throughout the tree.

Hardiness: The present tree was grown and evaluated in USDA Hardiness Zone 9. The calculated winter chilling requirements of the new tree is approximately 500 hours at a temperature below 7.0 degrees C. The present variety appears to be hardy under typical central San Joaquin Valley climatic conditions.

TRUNK

Diameter: Approximately 17.5 cm in diameter when measured at a distance of approximately 15.24 cm. above the soil level. This measurement was taken at the end of the 7th growing season.

Bark texture: Considered moderately rough, with folds of papery scarfskin being present. Since bark development, and coloration change with advancing tree age, this characteristic varies with the tree vigor, age, and regional environmental conditions. Therefore, this growing trait is not a dependable descriptor of the new variety.

Lenticels: Numerous flat, oval lenticels are present. The lenticels range in size from approximately 8.0 millimeters to about 10.0 mm. in width; and between about 1.0 and about 2.0 millimeters in height. The development and size of the trunk lenticels can be influenced, to some degree, by the ambient growing conditions, and are not, necessarily, a dependable characteristic of this variety. As trees of this variety mature, lenticels are present, but they are generally covered by increasing layers of cork (mature bark), and therefore become less apparent to an observer.

Lenticel color: Considered an orange-brown, (RHS Greyed-Orange Group 164 A).

Bark coloration: Variable, but it is generally considered to be a grey-brown, (Grey-Brown Group RHS N199 B). This bark description was taken from trees in their sixth leaf, and which have ruptured the scarf skin, and which further also have developed bark furrowing that is much more typical of the bark of older trees. It should be noted that the coloration of the bark is influenced, and varies, as the smoother, darker background color approaches other bark features such as the lenticels, and the initial fissures which form a feature of the scarf skin development.

BRANCHES

Size: Considered medium-large for the species.

Diameter: Average as compared to other peach tree varieties. The branches have a diameter of about 11.0 centimeters when measured during the 6th year after grafting.

Flowering shoot thickness: Approximately 8.5 mm.

Surface texture: Average, and appearing relatively smooth, but with more furrowing on wood which is several years old.

Crotch angles: Primary branches are considered variable, and are usually growing at an angle of about 42 to about 50 degrees when measured from a horizontal plane. This particular characteristic can vary due to influences such as variable ecological conditions, and the current cultural practices employed.

Current season shoots:

*Surface texture.*—Substantially glabrous.

Internode length: Approximately 2.4 cm.

Color of mature branches: Approximately Grey brown, (Greyed-Orange Group RHS 177 C).

Current season's shoots:

*Color.*—Light green, (Yellow-Green Group RHS 145 C). The color of new shoot tips is considered a bright and shiny green (Yellow-Green Group RHS 146 D). The vegetative shoot color can be significantly influenced by plant nutrition, irrigation practices, and exposure to sunlight, and therefore should not be considered a consistent botanical characteristic of this new variety of peach tree.

LEAVES

Size: Considered somewhat elongated, and narrow for the species. Leaf measurements have been taken from vigorous, upright, current-season growth, taken at approximately mid-shoot. It should be understood that the leaf size is often influenced by the prevailing growing conditions, quality of sunlight, and the growth location of the leaf within the tree canopy. For this reason, leaf sizes can vary, sometimes significantly, based upon the ambient, and other cultural factors listed above, and are not typically considered a dependable botanical descriptor.

Leaf length: Approximately 158.0 to about 168.0 millimeters.

Leaf width: Approximately 28.0 to about 32.0 millimeters.

Leaf base-shape: The leaves generally exhibit equal marginal symmetry relative to the longitudinal axis of the leaf.

Leaf form: Lanceolate.

Leaf tip form: Acuminate.

Leaf color:

*Upper and lower leaf surfaces.*—Medium green, (approximately Green Group RHS 137 B).

Leaf texture:

*Upper leaf surface.*—Glabrous.

*Lower leaf surface.*—Glabrous.

Leaf color:

*Lower leaf surface.*—Medium green, (approximately Green Group RHS 137 D).

Leaf venation: Pinnately veined.

Mid-vein:

*Color.*—Considered a light yellow, (approximately Greyed-Yellow Group RHS 160 C) when viewed in the early to mid-period of the growing season.

Leaf marginal form: Gently undulating.

*Marginal edge shape.*—Considered finely crenate.

*Uniformity.*—Considered generally uniform.

Leaf petioles:

*Form.*—Considered canaliculated, and having a more pronounced trough when viewed from the dorsal aspect. The petiole margin is considered rounded when viewed from the ventral aspect.

*Size.*—Considered medium-small for the species.

*Length.*—About 8.0 to about 11.0 mm.

*Diameter.*—About 1.5 to about 2.0 mm.

*Color.*—Light yellow green, (approximately RHS Yellow-Green Group 145 A).

*Surface texture.*—Substantially glabrous.

*Strength.*—The pedicle is considered durable for the species until senescence.

Leaf glands:

*Size.*—Considered relatively small for the species; approximately 2.0 mm. in length; and about 1.0 mm. in height.

*Number.*—Generally one and less common two glands appear per marginal side. Observations of more than two glands per marginal side are very uncommon.

*Type.*—Leaf glands located at the base of the leaf are predominantly reniform in shape. An additional one to two, or occasionally more leaf glands, which appear globose, and stalked, are often present at the basal margin of the leaf petiole as well.

*Color.*—Considered a medium-dark brown, approximately (RHS Brown Group 199 A). Typically the coloration of the glands darken, and occasionally begins to desiccate during the mid-late portion of the growing season.

Leaf stipules:

*Size.*—Medium large for this variety.

*Number.*—Typically 2 per leaf bud, and up to 6 per shoot tip.

*Form.*—Lanceolate, and having a serrated marginal edge.

*Color.*—Green, (approximately RHS Green Group 137 B) when young, but graduating to a brown color, (approximately RHS Greyed-Orange Group 165 A) with advancing senescence. The leaf stipules are generally considered to be early deciduous.

FLOWER BUDS

Hardiness: No winter injury (bud death) has been noted during the last several years of observation in the central San Joaquin Valley. The new variety of peach tree has not been intentionally subjected to drought, cold or heat stress, and therefore this information is not available.

Flower bud:

*Size.*—Variable, and dependent upon the state of maturity. The flower buds, as described, were observed approximately 7 days prior to bloom.

*Length.*—Approximately 15.5 millimeters.

*Diameter.*—Approximately 8.5 millimeters.

*Surface texture.*—Pubescent.

*Orientation.*—Considered appressed, but appearing less so as the blossoms near opening.

Bud scale color: Grey-orange, (approximately Greyed-Orange Group RHS 175 A).

FLOWERS

Date of first bloom: Observed on Feb. 20, 2016.

Blooming time: Considered average in relative comparison to other commercial peach cultivars grown in the central San Joaquin Valley. The date of full bloom was observed on Feb. 28, 2016. The date of full bloom varies slightly with climatic conditions, and the prevailing cultural practices which are empolyed.

Duration of bloom: Approximately 8 or more days. This particular characteristic varies slightly with the prevailing climatic conditions.

Flower class: Considered a perfect flower, complete and perigynous.

Flower type: The variety is considered to have a showy-type flower.

Flower size: Considered large for the species. The flower diameter, at full bloom, is approximately 57.0 to 60.0 millimeters.

Bloom quantity: Considered abundant.

Flower bud density: Generally considered dense.

Flower bud frequency: Generally two flower buds appear per node, occasionally one flower bud per node is observed. Very rarely three floral Bud's per node are observed.

Petal size: Generally considered large for the species.

Petal length: Approximately 26.0 to 28.0 millimeters.

Petal width: Approximately 21.0 to 26.0 millimeters.

Petal form: Considered broadly ovate.

Petal count: Nearly always 5.

Petal texture:

*Upper and lower petal textures.*—Very finely pubescent, and satin like.

Petal color: Considered a light pink at the popcorn stage, (RHS Red-Purple Group 65 B), and darkening with advancing senescence, and the exposure of sunlight, to a medium-dark pink, (RHS Red-Purple 63 C). This darkening of the petal is generally most present within the margins of the petal claw.

Fragrance: Slight.

Petal claw:

*Form.*—The petal claw is considered ovate, and is generally large.

*Length.*—Approximately 14.0 to16.0 millimeters.

*Width.*—Approximately 10.5 to 14.0 millimeters.

Petal margins: Generally the petal margins are moderately undulate in form and ruffled, especially apically.

Petal apex: Often the petal margins exhibit a shallow, and wide recess at tip.

Petal margin width: Approximately 2.5 to 4.0 millimeters.

Petal margin depth: About 1.0 to 2.0 millimeters.

Flower pedicel:

*Length.*—Considered medium-long, with an approximate length of about 1.5 to about 3.5 millimeters.

*Diameter.*—Approximately 2.5 millimeters.

*Color.*—A medium brown, approximately (RHS Grey-Brown Group N199 D). This color depends upon the pedicel, fruit maturity and timing of the visual observation.

*Strength.*—Tenacious. Considered average for the species.

*Surface texture.*—Generally smooth to slightly undulate.

Floral nectaries color: Considered a dull brown (approximately RHS Greyed-Orange Group 175 B).

Calyx:

*Surface texture.*—Generally glabrous.

*Color.*—A dull grey-purple, (approximately RHS Greyed-Purple Group 185 B).

Sepals:

*Upper and lower surface texture.*—Very finely pubescent.

*Numbers.*—5 sepals are typically seen.

*Size.*—Generally, medium-large for the species.

*Sepal length.*—Approximately 5.0 to 8.0 millimeters.

*Sepal width.*—Approximately 4.0 to 6.0 millimeters.

*Sepal shape.*—Generally obovate.

*Sepal margin.*—Considered smooth and entire.

*Sepal color.*—A dull grey purple, (approximately RHS Greyed-Green Group 197 B).

Anthers:

*Generally.*—Average in size.

*Anther color.*—Yellow, when viewed dorsally, and prior to dehiscence, (approximately RHS Greyed-Yellow Group 162 B).

*Anther position relative to the stigma.*—Generally the stigma is superior to the anthers by approx. 1.0-2.0 millimeters.

Pollen production: Pollen is abundant, and has a yellow color, (approximately RHS Yellow-Orange Group 18 A).

Fertility: Self-fertile.

Filaments:

*Size.*—Approximately 17.5 to 20.0 millimeters in length.

*Color.*—Considered Red-yellow, (RHS Red Yellow Group 11 D).

Pistil:

*Number.*—Usually one, and only rarely more than one.

Pistil size: Generally considered large in size.

Pistil length: Approximately 19.0 to about 22.0 millimeters in length, including the ovary.

Pistil color: Considered a very pale green, (approximately RHS Yellow-Green Group 154 D).

Pistil surface texture: The variety has a long pubescent pistil.

Stamen position relative to the petals: At flower maturity the stamens grow to be in a position which are superior to the petals.

FRUIT

Maturity when described: Firm ripe condition (shipping ripe).

Date of first picking: Approximately Jun. 12, 2016.

Date of last picking: Jun. 19, 2016. The date of harvest can vary with the prevailing climatic conditions, crop loads and the current climatic and cultural practices which are utilized.

Size:

*Generally*.—Considered medium-large for the species.

Average cheek diameter: Approximately 74.0 to about 79.0 millimeters.

Average axial diameter: Approximately 72.0 to about 77.0 millimeters.

Typical fruit weight: Approximately 215.0 grams. The aforementioned characteristics are quite dependent upon the prevailing cultural practices, and growing conditions, and therefore is not a particularly distinctive characteristic of the new variety.

Fruit form:

*Generally*.—Considered globose. The fruit is generally very uniform in symmetry.

Mucron tip: Absent.

Fruit suture:

*Generally*.—No stitching exists along the suture line.

Suture:

*Color*.—Generally, the fruit appears blushed to the same degree as the skin, (approximately RHS Orange-Red Group 34 A).

Ventral surface:

*Form*.—Considered even, and uniform in appearance, when it is viewed from the lateral, sutural plane.

Apex:

*Shape*.—Rounded to slightly rutuse.

Base:

*Shape*.—Generally smooth.

Stem cavity:

*Generally*.—The stem cavity extends in a rounded circular form which is generally considered uniform. The stem cavity is rounded but slightly extended toward the suture. The average depth of the stem cavity is about 8.0-10.0 mm. The average width of the stem cavity is about 26.0 mm. The average length of the stem cavity, when measured in the suturial plane is about 45.0 mm.

Fruit skin:

*Thickness*.—Considered medium in thickness, and tenacious to the flesh.

*Surface texture*.—A short and fine pubescence is present. The pubescence is moderately abundant.

*Taste*.—Non-astringent.

*Tendency to crack*.—Not observed in the previous years of observation, and evaluation.

Fruit skin color:

*Blush color*.—Generally speaking, a red blush exists on a majority of the skin surface of the fruit (approximately RHS Orange-Red Group 34 A). The blush is more typically present on the portions of the fruit facing the sunlight. Further, the blush of the fruit typically covers approximately 65%-85% of the fruit skin surface. The percentage of the blush on the fruit skin surface can vary, and is generally dependent upon the fruit's exposure to direct sunlight; specific fruit maturity; and also the prevailing ecological and cultural conditions under which the fruit was grown.

Ground color: A medium light orange-yellow, (approximately RHS Yellow-Orange Group 23 C). The ground color of the fruit can vary significantly based upon the maturity of the fruit when this measurement is taken, and generally gains or develops a lighter, and green cast with advancing maturity.

Fruit glossiness: The fruit is not considered to be glossy.

Fruit stem:

*Size*.—Medium in length, approximately 6.0 to about 8.0 millimeters.

*Diameter*.—Approximately 2.0 to about 3.0 millimeters.

*Color*.—Pale yellow-green, (approximately RHS Yellow-Green Group N144 C).

Fruit flesh:

*Ripening*.—Considered even.

*Texture*.—Firm, crunchy, juicy and dense. Considered firm-melting in flesh texture.

*Fibers*.—Present, but not prominent.

*Aroma*.—Slight.

*Eating quality*.—Considered very good.

*Flavor*.—Considered balanced with sweetness and acidity.

*Juice production*.—Moderate.

*Brix*.—About 11.0 to 13.5 degrees. This characteristic varies slightly with the number of fruit per tree; the maturity of fruit when harvested; the prevailing cultural practices; and the ambient climatic conditions under which the fruit was grown.

*Acidity*.—Considered low. Approximately 0.8 titratable acidity. Acid levels assayed from fruit flesh can vary based upon the fruit maturity, sunlight exposure, and climatic, regional and cultural influences or practices employed.

*Flesh color*.—It is considered yellow in color, (approximately RHS Yellow-Orange Group 17 D). A slight pigmentation of a pink-red color can be seen radiating from the stone (approximately RHS Red Group 39 A).

STONE

Type: Considered a clingstone.

Size: It is generally considered to be medium to small for the species. The stone size varies significantly depending upon the tree vigor, the crop load, and the prevailing growing and cultural conditions under which the tree was grown.

Stone length: Average, about 29.0 to about 32.0 millimeters.

Stone width: Average, about 21.0 to about 24.0 millimeters.

Stone diameter: Average, about 17.0 to about 20.0 millimeters.

Stone form: Roughly ovoid.

Stone base:

*Shape*.—The stone is considered shortly attenuate.

Stone apex:

*Shape*.—The stone exhibits a slightly acute apex.

Stone surface:

*Surface texture*.—Considered irregularly furrowed toward the apex. Further, more pitting exists in the mid-portion of the stone (laterally), and is more common toward the base.

*Ridges*.—Ridging is generally more prominent, and is usually oriented substantially parallel, and laterally relative to the ventral and dorsal margins.

*Ventral edge*.—The ventral edge is generally described as having adjoining ridges formed from each hemisphere. There are longitudinal grooves running alongside this joined ventral suture.

*Dorsal edge.*—Shape — Generally considered even. The folds of the surface ridges appearing on the external margins often end gently along the suture.

Stone color: The color of a mature, dry stone is generally considered a dull brown, approximately (RHS Greyed-Orange Group 165 D). The observed stone color can vary based upon how recently the fruit has ripened, the degree of oxidation which has taken place, and any blanching which has occurred due to the exposure sunlight.

Tendency to split: Splitting has only rarely been noted.

Kernel:

*Length.*—Approximately 14.0-17.0 millimeters.

*Width.*—Approximately 12.0-15.0 millimeters.

*Thickness.*—4.0-6.0 millimeters.

*Size.*—The kernel is considered medium in size.

*Form.*—Considered generally ovoid. The fruit of the current variety ripens before the kernel has had time to develop completely, is still gelatinous, and principally exhibits translucent cotyledons. Generally speaking, therefore, the consistency and form of the kernel varies. Often the kernel can shrivel, particularly at the base.

*Kernel surface texture.*—The kernel pellicle has a short pubescence.

*Color.*—A dark tan (RHS Greyed-Orange Group 165 C).

Use: The present variety 'Burpeachforty' is considered to be a peach tree of the late season of maturity, and which produces fruit which are considered to be firm, attractively colored, and which are useful for both local and long distance shipping.

Keeping quality: Appears excellent. The fruit of the present variety has stored well for periods of up to 35 days after harvest at 1.0 degree Celsius.

Shipping quality: Good. The fruit of the new peach tree variety showed minimal bruising of the flesh or skin damage after being subjected to normal harvesting and packing procedures.

Resistance to insects and disease: No particular susceptibilities were noted. The present variety has not been intentionally tested to expose or detect any susceptibilities or resistances to any known plant, fruit diseases, insect, frost, winter injury or other environmental factors.

Although the new variety of peach tree possesses the described characteristics when grown under the ecological conditions prevailing near Fowler, Calif., in the central part of the San Joaquin Valley of California, it should be understood that variations of the usual magnitude, and characteristics incident to changes in growing conditions, fertilization, nutrition, pruning, pest control, frost, climatic variables and changes in horticultural management are to be expected.

Having thus described and illustrated our new variety of peach tree, what we claim is new, and desire to secure by Plant Letters Patent is:

1. A new distinct variety of peach tree, substantially as illustrated and described, and which is characterized principally as to novelty by producing an attractively colored yellow fleshed, clingstone peach which is mature for harvesting and shipment approximately June 12 to June 19 under the ecological conditions prevailing in the San Joaquin Valley of central California.

* * * * *